United States Patent [19]

Sullivan et al.

[11] Patent Number: 5,391,383
[45] Date of Patent: * Feb. 21, 1995

[54] EDIBLE SPRAY OIL

[75] Inventors: Joanne Sullivan, Wyckoff; Michael M. Chrysam, Blairstown, both of N.J.

[73] Assignee: Nabisco, Inc., Parsippany, N.J.

[*] Notice: The portion of the term of this patent subsequent to Jan. 3, 2012 has been disclaimed.

[21] Appl. No.: 7,447

[22] Filed: Jan. 22, 1993

Related U.S. Application Data

[63] Continuation-in-part of Ser. No. 804,140, Dec. 6, 1991, Pat. No. 5,258,197, which is a continuation-in-part of Ser. No. 624,056, Dec. 7, 1990, abandoned, which is a continuation-in-part of Ser. No. 410,161, Sep. 20, 1989, abandoned.

[51] Int. Cl.$^6$ ............... A23D 9/00; A23P 1/08
[52] U.S. Cl. .................. 426/99; 426/96; 426/291; 426/303; 426/804
[58] Field of Search .......... 426/804, 303, 89, 96, 426/99, 291

[56] References Cited

U.S. PATENT DOCUMENTS

| | | |
|---|---|---|
| 3,536,035 | 10/1970 | Watkins . |
| 3,876,811 | 4/1975 | Bonner .................... 426/96 |
| 4,251,551 | 2/1981 | VanHulle et al. . |
| 4,501,758 | 2/1985 | Morris . |
| 4,517,204 | 5/1985 | Mottur et al. . |
| 4,743,456 | 5/1988 | Spadafora . |
| 4,767,636 | 9/1988 | Rothenberg et al. . |
| 4,769,247 | 8/1988 | Ramos . |
| 4,849,233 | 7/1989 | Hemker . |
| 5,015,484 | 5/1991 | Palmlin .................... 426/96 |

OTHER PUBLICATIONS

Bailey's Industrial Oil and Fat Products, vol. 3, John Wiley (1985).
Bonanome, A. and Grundy, S. M., New Eng. Jour. Med. 318: 1244–1248 (1988).

*Primary Examiner*—Carolyn Paden

[57] ABSTRACT

Non-greasy spray oils for snack and other food products are especially useful for adhering topical seasonings or condiments to the products. The spray oils contain fats bearing short acetic acid, propionic and/or butyric acid residues, and long, saturated $C_{16}$ to $C_{24}$ fatty acid residues. Especially preferred are triglycerides exhibiting a solid fat index at 70° F. of at least about 50%, more preferably at least about 60%, and at least about 40%, more preferably at least about 50%, at 80° F. One preferred embodiment contains triglycerides wherein at least about 75% of the long acid residues are stearic acid or longer residues and the short residues are mixtures of acetic acid and propionic acid residues, acetic acid and butyric acid residues, or a mixture of acetic acid, propionic acid, and butyric acid residues. The spray oils are low in calories and oxidation resistant.

28 Claims, No Drawings

EDIBLE SPRAY OIL

RELATED U.S. APPLICATION DATA

This is a continuation-in-part of U.S. application Ser. No. 804,140, filed Dec. 6, 1991, now U.S. Pat. No. 5,258,197, hereby incorporated in its entirety by reference, which was a continuation-in-part of U.S. application Ser. No. 07/624,056, filed Dec. 7, 1990, now abandoned, which was a continuation-in-part of U.S. application Ser. No. 07/410,161, filed on Sep. 20, 1989, now abandoned.

TECHNICAL FIELD

The invention relates to spray oils of the type used to enhance the organoleptic character of foods, including crackers, nuts, chips, and puffed and other snack items and has special advantage for foods which have particulate flavorings and/or seasonings applied to the exterior.

The eating qualilty, flavor and appearance of crackers are enhanced by the application of an oil as a spray. The spray is often applied while the crackers are still warm from baking. A portion of the oil should penetrate into the cracker to improve the bite and mouthfeel, and a portion should remain on the surface to provide a desirable sheen. Preferred oils are solid or plastic at room temperature, e.g., 20° C., but become liquid below body temperature, e.g., 37° C. Unfortunately, these fats tend to stain packaging and cause greasiness on the hands. This is a particular problem when the spray oils are employed in amounts sufficient to bind particulate seasonings and flavors to crackers and snack products.

BACKGROUND OF THE INVENTION

A variety of spray oils and coating processes have been suggested for snack, cracker and other food products. Hydrogenated coconut oil is a preferred spray oil; however, partially hydrogenated peanut oil and soybean oil are also used (*Bailey's Industrial Oil and Fat Products*, vol. 3, John Wiley, 1985, page 109). These typically leave a greasy residue on hands and paper goods in contact with sprayed products, and, where the products are seasoned, the seasoning comes off with handling.

In U.S. Pat. No. 4,767,636, Ramos, et al., disclose a process for manufacturing an instant rice and sauce dish which involves coating the rice with partially hydrogenated vegetable oil, contacting the oil coated rice with dry ingredients, applying a second layer of oil to the coated rice, and then applying a third layer of oil to hold the seasonings firmly in place. Likewise, Rothenberg, et al., suggested that pasta be heated to 100° to 140° F., coated with melted hydrogenated fat in a tumbler, and contacted and mixed with dry ingredients, prior to applying a second and then a third coat of fat (U.S. Pat. No. 4,769,247). Both disclosures employ multiple processing steps to affix seasoning to the product.

Other disclosures instead favor selecting special ingredients to achieve a similar result. For example, flavoring material such as cheese and salt was mixed with vegetable oils (containing, for example, cottonseed oil, soybean oil, and the like) and applied as a slurry on reduced calorie puffed snack products containing hydrophilic polysaccharide coated microcrystalline cellulose in U.S. Pat. No. 4,517,204 to Mottur and Glass. Alternatively, in U.S. Pat. No. 4,251,551 to VanHulle, et al., puffed snack products were prepared by enrobing gelatinized, partially dry dough pellets with a triglyceride component (coconut oil, soybean oil, cottonseed oil, peanut oil, sesame seed oil, sunflower seed, or palm oil) and then a dry mixture of dehydrated cheese solids (with optional puffing medium ingredients) prior to cooking in a microwave oven. Hemker suggested that an edible coating composition for popcorn be formulated with a high sweeteners solids level along with a hydrophilic film former (e.g., gelatin, egg albumin, etc.) and a high fat component level (U.S. Pat. No. 4,849,233).

Elimination of adherent oil was suggested for snack foods such as potato chips, corn chips, potato products and grain cereals if their coating condiments were subjected to an electrostatic field subjected so as to impart a particular charge whereby they are attracted to the snacks (U.S. Pat. No. 3,536,035 to Watkins), but the disclosure involved specialized equipment. A sugar and carbohydrate adhesive was applied prior to applying a honey-containing dry mixture to nuts (U.S. Pat. No. 4,501,758 to Morris), but the process was directed to the production of honey coated nuts and not other types of coatings.

It would be desirable to affix seasonings to sprayed food products without the use of multiple processing steps, additional binder ingredients, or specialized equipment. It would also be desirable to provide non-greasy sprayed snack products that could be touched without soiling the hands or stored in paper or cardboard without soiling the container, yet provide good eating quality.

DISCLOSURE OF THE INVENTION

An object of the present invention is to provide a new group of edible spray oils especially useful for snack and other food products.

It is another object of the invention to provide spray oils for cracker, snack and other food products that provide acceptable mouthmelt yet are not greasy, so that their handfeel is less messy, and the products can be stored in ecologically desirable biodegradable containers without staining them.

It is a further object of the invention to provide, for cracker, snack, and other food products having exteriorly applied seasonings or condiments, especially adherent spray oils.

These and other objects are accomplished by the present invention, which provides spray oils that are non-greasy, quick-setting, transparent, and adherent. The spray oils comprise triglycerides bearing $C_2$ to $C_4$ short acid residues and long $C_{16}$ to $C_{22}$ saturated fatty acid residues. Especially preferred are triglycerides exhibiting a solid fat index at 70° F. of at least about 50%, more preferably at least about 60%, and at least about 40%, more preferably at least about 50%, at 80° F. Preferred embodiments contain triglycerides wherein at least about 75% of the long acid residues are stearic acid residues, and the short residues are derived from propionic acid, mixtures of acetic acid and propionic acid, butyric acid, mixtures of acetic acid and butyric acid, mixtures of propionic acid and butyric acid, and mixtures of acetic acid, propionic acid, and butyric acid. One particularly preferred embodiment contains fats bearing the same complement of long residues, such as, for example, long residues derived from hydrogenated canola, hydrogenated soybean oil, or tristearin, and short residues derived from a mixture of acetic acid and propionic acid.

Food, particularly snack, products improved with the spray oils of this invention are disclosed. These products lack the greasiness of typical snacks prepared with conventional spray oils, so that handling and storage of the products is less messy. Where snacks dusted or coated with seasonings, these adhere well. In addition, snacks prepared with the spray oils of this invention are lower in calories than typical snacks prepared with conventional fats, and more oxidation resistant.

Methods for adhering seasonings to food products are also disclosed.

GENERAL DESCRIPTION OF THE INVENTION

The spray oils of this invention are enriched with triglycerides having both long, saturated $C_{16}$ to $C_{24}$ fatty acid residues and short $C_2$ to $C_4$ acid residues (hereafter referred to as "short/long triglycerides"). Especially preferred are triglycerides having a solid fat index of at least about 50%, more preferably at least about 60%, at 70° F., and at least about 40%, more preferably at least about 50%, at 80° F.

Most preferably, the long fatty acid residues will be predominantly, i.e., at least about 75%, and in some embodiments at least about 90% $C_{18}$ to $C_{24}$, and the short acid residues will be a mixture of $C_2$ and $C_3$, $C_2$ and $C_4$, or $C_2$ to $C_4$.

Denoting the aliphatic portion of the long fatty acid substituent as L and the short as S, the spray oils of this invention contain fats comprising a mixture of SSL, SLS, LLS, and LSL species described by the following formulae:

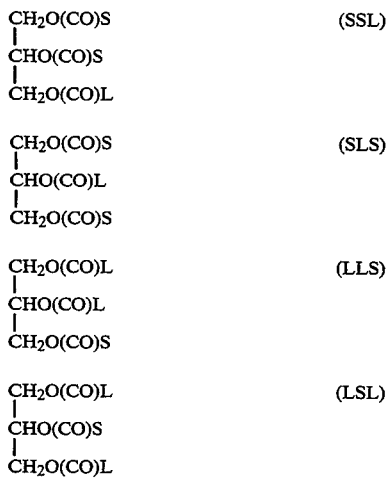

where
each L, independently, is a long chain saturated aliphatic group having between 15 and 23 carbons, derived from a fatty acid having 16 and 24 carbons; and
and
each S, independently, is a short chain group having 1 to 3 carbons, derived from an acid having 2 to 4 carbons.

Depending upon the preparative procedure, the triglyceride mixtures may also contain triglycerides of the formulae

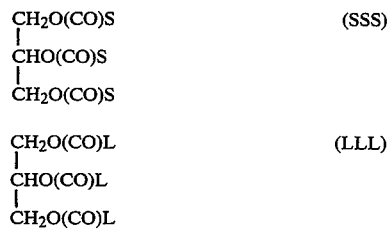

where S and L are as defined above.

However, preferred mixtures contain essentially no SSS and less than 3% preferably less than 2%, LLL.

Short acid residues have 2 to 4 carbons. Short residues are derived from carboxylic acids of the formula SCOOH, where S is a short chain aliphatic group having 1 to 3 carbons. As denoted herein, where triglycerides are described as bearing pendant groups derived from acids having 2, 3, or 4 carbons, compositions derived from acids having predominantly 2, 3, or 4 carbons are included. Acylation of a glycerol hydroxyl by acid SCOOH results in the attachment of short chain S to the glycerol backbone by means of an ester linkage (—O—(CO)—). Where there is more than one short group attached to a glyceride, the groups may be the same or different. As used herein, the term "acid residue" refers to an acyl group comprising a short chain portion, here S, and a carbonyl group.

Short chain S may be straight or branched. Short chain S may be derived from any synthetic or natural organic acid including, but not limited to acetic (ethanoic), propionic (propanoic), butyric (butanoic), and the like acids. As used herein, chemical names include isomeric variations; for example, "butyric acid" includes normal-butyric acid (butanoic) and iso-butyric (2-methylpropanoic) acid, and so forth. Preferred acids are acetic, propionic, and butyric acids, and mixtures of these.

The long saturated pendant groups are derived from fatty acids of the formula LCOOH, where L is a saturated aliphatic group having 15 to 23 carbons. L groups may be derived from any synthetic or natural, straight or branched saturated organic acid including, but not limited to, palmitic (hexadecanoic), stearic (octadecanoic), arachidic (eicosanoic), behenic (docosanoic), and the like acids.

L groups may be derived by hydrogenating unsaturated acid of the formula UCOOH, where U is a $C_{15}$ to $C_{21}$ unsaturated group, including, but not limited to, palmitoleic (9-hexadecenoic), oleic (cis-9-octadecenoic), elaidic (trans-9-octadecenoic), vaccenic (trans-11-octadecenoic), linoleic (cis, cis-9,12-octadecadienoic), linolenic (9,12,15-octadecatrienoic and 6,9,12-octadecatrienoic), eleostearic (9,11,13-octadecatrienoic), arachidonic (5,8,11,14-eicosatetraenoic), erucic (cis-13-docosenoic) and the like acids.

The various L and U groups can be derived from mixtures of fatty acids obtained from natural oils such as soybean, safflower, sunflower, sesame, peanut, corn, olive, rice bran, mustard seed, cottonseed, poppyseed, rapeseed, marine, meadowfoam and the like oils; fats such as babassu nut oil, palm oil, palm kernel oil, tallow, lard, shea butter, and dairy butter; or plant waxes such as jojoba. Fat mixtures and/or fractions, crystallized fats, interesterified fats and mixtures of these may also be employed.

Mixtures of L groups are preferably derived from oils and fats that are hydrogenated, most preferably fully hydrogenated. Hydrogenated fats having at least about 70%, preferably at least about 75%, stearic acid residues such as, for example, hydrogenated peanut oil, hydrogenated olive oil, hydrogenated soybean oil, hydrogenated sesame oil, and hydrogenated corn oil are especially desirable for some embodiments. Other embodiments employ L moieties derived from hydrogenated fats having at least about 90% stearic acid residues, such as hydrogenated sunflower oil, hydrogenated safflower oil and hydrogenated canola. Some embodiments employ hydrogenated feedstocks bearing predominantly $C_{18}$ to $C_{24}$ acid residues such as, for example, hydrogenated high erucic rapeseed, hydrogenated meadowfoam, and hydrogenated marine oils. For reasons more fully set out in the next section, preferred hydrogenated feedstocks are low in palmitic acid.

Component triglycerides making up the spray oils of this invention may be prepared using synthetic procedures known to those skilled in the art, such as, for example, directly esterifying glycerol or glycerol esters with fatty acids, fatty acid halides (notably chlorides) or fatty acid anhydrides, transesterifying glycerol with fatty acid esters, or interesterifying long and short chain triglycerides for such time and under such conditions that triglycerides bearing long and short residues form. Starting materials for triglyceride preparations may be obtained commercially or isolated from natural sources. Alternatively, component triglycerides may be isolated from natural or processed fats or oils, or fractions thereof.

Some desirable triglyceride mixtures are prepared using a random interesterification of triacetin, tripropionin and/or tributyrin with a substantially hydrogenated fat having predominantly stearic acid residues. For example, spray oils of this invention can be derived by the random interesterification of triacetin and tripropionin with hydrogenated canola, hydrogenated soybean oil, or tristearin, or the random interesterification of triacetin and tributyrin with the same long chain fats. Mixtures and fractions of triglycerides may also be employed. Example preparations are illustrated hereafter.

Isolated or prepared triglycerides are purified using techniques known to those skilled in the art. These include, but are not limited to, steam deodorization, fractional crystallization, distillation, chromatography, and the like. Example purifications are illustrated hereafter.

BEST MODES FOR CARRYING OUT THE INVENTION

In the practice of this invention, short/long triglycerides, fats bearing short $C_2$ to $C_4$ acid residues and long, saturated $C_{16}$ to $C_{24}$ fatty acid residues as defined above, and having a solid fat index of at least about 50%, preferably at least about 60%, at 70° F., and at least about 40%, preferably at least about 50% at 80° F. are warmed, sprayed onto a warmed food product substrate, and then cooled. Where seasonings are applied to the product, these may be dusted on before or after spraying on the oil, or mixed with the oil and applied to the food substrate as a slurry. Using either method, an additional spray oil coating may be applied to achieve greater seasoning adherence.

As used herein, the "solid fat index" of desirable spray oils of this invention refers to the percentage of a fat that exists in crystalline form at a given temperature. Solid fat indices (herein abbreviated S.F.I.) are determined using dilatometry according to A.O.C.S. Method Cd 10-57, and are reported at 50° F. (10° C.), 70° F. (21.1° C.), 80° F. (26.7° C.), 92° F. (33.3° C.), and 100° F. (37.8° C.).

The spray oils of this invention can be used alone, or in combination with another fat or fat mimetic. The oils can be used as the sole exteriorly applied oil or as a blend, or, where multiple coats are applied, as a final, non-greasy topcoat. Where spray oils are used on snack products having a greasy handfeel when made with conventional spray oils, the oils of this invention are employed in amounts effective to minimize or eliminate the greasy handfeel. When employed on food products to which seasonings or condiments are applied, the spray oils are desirably used in amounts effective to provide significant seasoning adherence. Preferred embodiments employ at least about 50% preferably 75% to 100%, long/short triglycerides having an S.F.I. of at least about 60% at 70° F. and at least about 50% at 80° F. as the sole spray oil or as the spray oil topcoat.

Spray oils should have an acceptable mouthmelt, preferably a pleasant organoleptic sensation when consumed, so preferred oils exhibit less than about 5% solids at 100° F., preferably less than about 1% solids at 100° F. This restriction does not apply to some high fat substrates, however, because the substrate may soften the coating.

Broadly speaking, the spray oils of this invention can be employed on a variety of food products having an exterior oil application or a fat coating. Food products prepared using spray oils of the invention have a solid substrate to which the oil is applied, and, for snack products, this substrate typically has a starch, nut or fruit component. Starches include, but are not limited to, wheat flour, rye flour, rice or rice flour, other cereals such as corn or oats (whole or milled), potato chips or flour, and the like. Prepared snack substrates may additionally have an aqueous component of water, milk, fruit juice or other liquid and/or a fat component. Short/long triglycerides can comprise all or part of the fat component in these embodiments as well as the spray oil. The products can also contain other ingredients known to those skilled in the art such as leavening or puffing ingredients, salt, other seasonings and flavorings, eggs, and the like. Prepared substrates for the spray oil are typically baked, roasted, or, in the case of popcorn, popped prior to oil application.

For most food products, the spray oil formulated using the short/long triglycerides is warmed to about 120° F. to about 160° F. and applied to the food substrate, which may also be warmed or coated warm out of the oven. Oil application is generally effected using sprayers, coating rollers, fluidized beds, or the like equipment known to the skilled artesan. The oil can be applied neat, as an emulsion or as a slurry. Where seasonings or condiments are to be applied, these may be dusted, blown or sprinkled on before or after oil application, or fed into a hopper that tumbles the food gently to coat all the surfaces before the oil is fully cooled. Alternatively, the warm oil can be mixed with seasonings or condiments, and the seasoning-oil mixture applied. Second, third, and subsequent coats of oil can be applied after cooling the first, but these are not required in most embodiments.

The thickness of the oil coating is determined by the temperature of both the food and the oil, by the viscosity and solids profile of the coating, by the speed of air in the air blowers (where these are employed in the cooling and/or dusting equipment), by the rate of cooling, and by the number of applications used. Preferred snack coatings are thin, translucent, and slightly glossy. Example formulations are given in the next sections.

Food products coated with the spray oils of this invention exhibit a number of desirable characteristics. An important advantage of the invention is that the messy handfeel of many snack products such as potato chips or cheese balls can be minimized or eliminated because preferred spray oils are extremely non-greasy after cooling. As has been mentioned, this enables preferred products to be stored in ecologically desirable recyclable paper containers, and, for pet foods, in thinner bags. Preferred products do not stain the bags.

Preferred short/long triglycerides set up fast to form a thin, durable coating that extends freshness by providing a moisture barrier, while improving eating quality and appearance. Sprayed breakfast cereals formulated with or without dextrin are hydration-resistant. Where seasonings are employed, the fast set simplifies the cooling step in manufacture, shortens preparation time, and facilitates, where desired, the application of multiple coats. Products with seasonings also exhibit good adherence, and, where coarse condiments are employed, they can be applied to the products without resorting to extra bonding layers or special pressure equipment.

Another advantage of the invention is that the spray oils are oxidation resistant. Because crackers, snacks, and other foods commonly sprayed have a large surface area, it is very important that a stable oil be used. As a topcoat, the spray oils of this invention can improve the shelf life of products sprayed with undercoats of other oils such as pet foods.

Another advantage of the invention is that the use of hydrogenated coconut oil, a preferred spray oil, can be minimized or eliminated from the sprayed food products. Coconut oil is a lauric fat having a fatty acid composition that includes significant quantities of lauric, myristic, and palmitic acid, saturated acids which have been shown to increase plasma cholesterol concentrations (Bonanome, A., and Grundy, S. M., *New Eng. Jour. Med.* 318: 1244–1248 (1988)).

Another advantage of the invention is calorie reduction in the final product. Spray oils on foods contribute significantly to the calories. The coating on sprayed crackers, for example, amounts to about 20% of the cracker weight (*Bailey's*, cited above), and oils have twice the caloric density of either carbohydrates or protein. Since the oils of this invention are low in calories, their use on foods reduces calories, and this effect can be enhanced by employing low calorie fats or fat mimetics in sprayed food substrates.

EXAMPLES

The following examples are presented to further illustrate and explain the present invention and should not be taken as limiting in any regard. Unless otherwise indicated, all parts and percentages are by weight, and are based on the weight at the particular stage of the processing being described. Solid fat indices (S.F.I. as denoted above) are determined using dilatometry according to A.O.C.S. Method Cd 10-57 (1989); solid fat contents (S.F.C.) of the products are determined using nuclear magnetic resonance (NMR) using A.O.C.S. method 16-81, both methods reporting solids at 50° F. (10° C.), 70° F. (21.1° C.), 80° F. (26.7° C.), 92° F. (33.3° C.), and 100° F. (37.8° C.). Mettler dropping points (M.D.P.) are determined using a Mettler Thermosystem FP 800 following A.O.C.S. Method Cc 18-80 (1989).

Fatty acid analyses are determined using proton NMR. In a typical NMR spectrum at 300 MegaHertz or higher, the long acid methyl resonance occurs farthest upfield, at $\sim 0.9$ ppm, as a triplet. The short acid methyl resonance is structure dependent and occurs at $\sim 2.00$ ppm (acetyl groups), $\sim 1.15$ ppm (propionyl groups) and $\sim 0.95$ ppm (butyryl groups).

Fat product analysis utilizes supercritical fluid chromatography (S.C.C.), which separates and quantifies fat mixture components according to their extent of fat migration. After filtering through a 0.45 micron filter, 0.1 $\mu$l of a 30 to 50 mg/ml sample is injected onto a $1 \times 100$ mm Deltabond Cyano ® column from Keystone Scientific in a Suprex Model 200A S.F.C. having an S.F.C.-grade carbon dioxide mobile phase and an oven temperature of 115° to 125° C. A linear pressure gradient of 100 to 300 atmospheres is applied over a course of 20 minutes (i.e., 10 atm/min), followed by a hold at 300 atmospheres for 10 minutes. A flame ionization detector at 375° to 400° C. detects emerging mixture components run against an internal standard of methyl tetradecanoate (10 to 12 mg/mL) in methylene chloride. External standards ($\sim 10$ mg/mL each) are run under identical conditions. Using these peak areas, the peak areas of the sample are normalized, added together, and divided by the total to obtain percentages of SSL/SLS, LLS/LSL, and LLL species in the mixtures.

Example 1

In this example, seasoned crackers are prepared using several spray oils of this invention, and the results are compared with crackers having a partially hydrogenated soybean spray oil control.

Preparation of the Spray oils

Spray oils of this invention are prepared by interesterifying one molar equivalent of refined canola (low erucic rapeseed oil containing 4% palmitic acid, 899 g/mole) hydrogenated at 180° C. and 60 lbs hydrogen until the Iodine Value (IV) is $\leq 3$ with the different molar equivalents of triacetin and tripropionin set out below. The reactants are interesterified in the presence of 0.2 to 0.3% sodium methoxide by heating to $\sim 110°$ C. with agitation under a vacuum for about half an hour until color develops. (The M.D.P. may be checked at this time, and the reaction continued if the M.D.P. has not dropped sufficiently.) Phosphoric acid ($\sim 0.2$ to $\sim 0.5\%$, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for $\frac{1}{2}$ to 1 hour at 110° C. The products are cooled to 80° C., filtered, bleached, and steam deodorized at 210° C. for 2 to 3 hours.

Six molar equivalents of triacetin and 6 molar equivalents of tripropionin are interesterified with hydrogenated canola and steam deodorized to yield fat product A. One molar equivalent of triacetin and 11 molar equivalents of tripropionin are interesterified with hydrogenated canola and steam deodorized to yield fat product B. Eleven molar equivalents of triacetin and 1 molar equivalent of tripropionin are interesterified with hydrogenated canola and steam deodorized to yield fat product C.

The products exhibit the following physical properties:

| Triacetin:Tripropionin:Hyrogenated Canola Reactant Molar Ratio | | | |
|---|---|---|---|
| | 6:6:1 A | 1:11:1 B | 11:1:1 C |
| M.D.P., °C. | 34.2° | 17.6° | 35° |
| S.F.C. 50° F. | 77.6% | 68.1% | 82.1% |
| 70° F. | 61.2% | 43.0% | 78.4% |
| 80° F. | 44.0% | 5.1% | 71.7% |
| 92° F. | 1.1% | 3.8% | 29.9% |
| 100° F. | 0.8% | 4.7% | 4.9% |

S.C.C. analysis of fat product B shows it to contain 82.3% SSL/SLS, 15.7% LLS/LSL, and 2.0% LLL species. Fatty acid analysis shows it to contain 7% acetic, 57% propionic, and 36% long chain residues.

S.C.C. analysis of fat product C shows it to contain 83.7% SSL/SLS, 15.2% LLS/LSL, and 0.9% LLL species. Fatty acid analysis shows it to contain 51% acetic, 13% propionic, and 36% long chain residues.

Fat product D is prepared by interesterifying 0.5 molar equivalent of triacetin, 1 molar equivalent of tripropionin, and 1 molar equivalent tributyrin with hydrogenated canola using the same procedure, followed by steam deodorization. The resulting product has an M.D.P. of 35° C. and an S.F.I. of 68.6% at 50° F., 63.2% at 70° F., 42.5% at 80° F., 4.6% at 92° F., and 4.6% at 100° F. Fatty acid analysis shows the fat to contain 11% acetic, 24% propionic, 24% butyric, and 41% long acid residues.

Cracker treatment and comparison

Identical chemically leavened wheat crackers (~14 g/each) are warmed at 250° F. for 2 to 3 minutes, dusted with a seasoning powder or particulates and then sprayed with test or control oil heated to 110°–120° F. using a Wagner paint sprayer (16% and 24% applications). The crackers are evaluated after cooling and then warmed in an oven to melt the oil coating, cooled, and again evaluated for appearance and messiness on the hands.

Using this procedure, the soybean oil-coated cracker had a messy hand feel before and after rewarming. Crackers coated with fat product A exhibited a transparent thin film and reduced messiness upon cooling, but messiness increased somewhat after rewarming (though the film remained). Crackers coated with fat product B were similar to the soybean controls. Crackers coated with fat product C exhibited an opaque, waxy snowflake-like coating upon cooling, and a transparent thin film with reduced messiness after rewarming. Crackers coated with fat product D exhibited a heavy opaque, waxy snowflake-like coating upon cooling, and a transparent thin film and reduced messiness after rewarming.

Example 2

In this example, crackers coated with several spray oils of this invention are compared to control crackers coated with partially hydrogenated soybean oil.

Preparation of the spray oils

Spray oils are prepared and purified as outlined in Example 1 above, except that hydrogenated soybean oil is employed instead of hydrogenated canola as an interesterification reactant.

Eleven molar equivalents of triacetin and 1 molar equivalent of tripropionin are interesterified with hydrogenated soybean oil and steam deodorized to yield fat product E. Fat product F is prepared by interesterifying 2.5 molar equivalents tributyrin with 1 molar equivalent hydrogenated soybean oil and steam deodorizing. Fat product G is prepared by interesterifying 1.5 molar equivalents of triacetin and 1.5 molar equivalents of tripropionin with 1 mole hydrogenated soybean oil and steam deodorizing.

The products exhibit the following physical properties:

| | Fat Product | | |
|---|---|---|---|
| | E | F | G |
| M.D.P., °C. | 34.3° | 33.2° | 36.0° |
| S.F.I. 50° F. | 69.5% | 66.8% | 71.9% |
| 70° F. | 68.3% | 36.9% | 71.0% |
| 80° F. | 63.9% | 12.2% | 64.7% |
| 92° F. | 1.2% | 7.7% | 7.0% |
| 100° F. | 0 | 6.9% | 3.2% |

Eleven molar equivalents of triacetin and 1 molar equivalent of tripropionin are interesterified with high oleic sunflower oil and steam deodorized to yield liquid fat product H, which has no solids between 32° and 100° F.

Cracker treatment and comparison

Chemically leavened wheat crackers are prepared by mixing

| ingredient | % |
|---|---|
| flour and malt flour | 62.8 |
| water | 21.9 |
| fat product F | 7.4 |
| sugar and corn syrup | 5.6 |
| soda and salt | 1.19 |
| calcium phosphate | 0.70 |
| ammonium bicarbonate | 0.46 |
| enzymes | 0.06 | sheeting and baking in the usual manner. A control cracker is prepared using soybean oil instead of fat product F. Before baking, the doughs are similar in appearance, structure, and machining, although the texture of the dough made with fat product F is slightly firmer. After baking, with spray oil and seasoning coating, there were no noticeable differences between crackers made with test fat shortening F and those made with soybean oil shortening. All the crackers had soft, tender and flaky textures.

Approximately 15% of fat products E, F, G, H, and soybean oil are applied warm (120°–140° F.) to crackers warmed at 250° F. for 2 to 3 minutes. Crackers coated with fat product H functioned much like a partially hydrogenated soybean spray oil control, and produced a translucent, slightly glossy products much like the control.

Crackers coated with fat product F formed a very light, very slightly opaque film, and had a pleasant flavor and eating quality, but did not provide the benefit of film formation and reduced messiness to the hands achieved with other test fats in the series. Crackers coated with fat products E and G formed heavier film with a nice mouthmelt. All three fats produced translucent, slightly glossy products, which improved the mouthfeel, moistness, and eating quality of the crackers, and reduced messiness on the hands as compared to crackers sprayed with control oils.

Example 3

In this example, the seasoning adhesive qualities of topical spray fat products E, F, and G prepared in Example 2 are compared with a soybean control spray oil. The oils are topically applied to a corn-based extruded snack at different load levels.

The oils are sprayed warm (120° to 140° F.) onto warmed extruded snacks. Natural salsa seasoning (from Fries and Fries, #221693) is dusted onto the tops, and spray oil applied using a Wagner paint sprayer. Sprayed product is then placed in a warm oven for 15 to 30 seconds to provide additional melting.

At all levels tested, 2.5% seasoning and 10% oil, 2.5% seasoning and 20% oil, and 5% seasoning and 5% oil, fat product E adhered the seasoning to the corn chip very well and formed nongreasy thin films that eliminated the oily messy handfeel of the controls (2.5% seasoning and 7% soybean oil, 5% seasoning and 15% oil). Similarly, at all levels tested, 2.5% seasoning and 10% oil, 5% seasoning and 10% oil, and 5% seasoning and 15% oil, fat product G adhered the seasoning to the extruded snack and formed nongreasy thin films. Both products yielded extruded snacks with good mouthmelt, moistness, lubricity and overall eating quality.

Extruded snacks coated with fat product F, at levels of 2.5% seasoning and 10% oil, were slightly more opaque and exhibited a slightly messier handfeel than that observed with products E and G, and not as messy to the hands as soybean oil-coated controls. The eating quality was unimpaired.

Example 4

This example illustrates that spray oils of this invention can be applied in a slurry with condiments or seasonings. Cheese balls are prepared.

Fat product F of Example 2 is distilled using a Pope® 2" wipe film still configured for molecular distillation. The still body temperature is 260° C., the inner condenser temperature is 73° C., the vacuum is 0.05 to 0.03 mm Hg, and the wiper speed is 161 rpm, reverse mode. Chromatographic analysis of the distillate fraction show that the product, denoted fat product I, contains no LLL species, whereas the residue does.

An extruded corn meal ball (prepared with corn masa injected with 16% water), 51.64%, is coated with about 48.36% of a slurry composed of 35.22% fat product I, 10.7% cheese powder and 2.44% salt. The coating has the flavor, appearance, color and mouthfeel of a control cheese ball coated with a slurry of 75%:25% hydrogenated soybean:hydrogenated cottonseed oil (hydrogenated to an IV of 75 to 80 and having a Wiley melting point of 95° F.), but is lower in calories.

Example 5

A baked potato-based chip is sprayed with melted fat product C of Example 1. The fat crystallized as a translucent white powder which, on heating, formed a solid, transparent, somewhat glossy coating. The product is not greasy, and has a good mouth and handfeel. Dusting the same chip with Fidco Cajun #WP66-52 barbecue seasoning prior to spraying results in a snack product having good adherence as well.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

We claim:

1. A food product prepared by spray-coating an edible substrate with a spray oil comprising at least 50% low-calorie triglycerides bearing both $C_2$ to $C_4$ short acid residues and long $C_{16}$ to $C_{24}$ saturated fatty acid residues, wherein the oil has a solid fat index of at least about 50% at 70° F. and at least about 40% at 80° F.

2. A product according to claim 1 wherein the oil has a solid fat index of at least about 60% at 70° F. and at least about 50% at 80° F.

3. A product according to claim 1 wherein the short acid residues in the triglycerides are derived from acetic acid, propionic acid, butyric acid, or mixtures of these, and at least 75% of the long fatty acid residues are $C_{18}$ to $C_{24}$ acid residues.

4. A product according to claim 3 wherein the short acid residues are derived from a mixture of acetic acid and propionic acid.

5. A product according to claim 3 wherein at least about 90% of the long fatty acids are stearic acid residues.

6. A product according to claim 3 wherein the long acid residues are derived from hydrogenated oils selected from the group consisting of hydrogenated soybean oil, hydrogenated canola, hydrogenated high erucic rapeseed, and hydrogenated meadowfoam.

7. A product according to claim 3 comprising triglycerides prepared by the random interesterification of hydrogenated canola, hydrogenated soybean oil or tristearin and short chain reactants selected from the group consisting of:
(a) a mixture of triacetin and tripropionin;
(b) a mixture of triacetin and tributyrin;
(c) a mixture of triacetin, tripropionin, and tributyrin;
(d) tributyrin; and
(e) mixtures of these.

8. A product according to claim 7 prepared by the random interesterification of 1 molar equivalent of hydrogenated canola, hydrogenated soybean oil or tristearin with 12 molar equivalents of a mixture of triacetin and tripropionin.

9. A product according to claim 1 to which topical seasonings are applied before or after coating with said triglycerides or applied as a mixture with said triglycerides.

10. A product according to claim 9 wherein the substrate comprises a starch ingredient.

11. A product according to claim 1 wherein the edible substrate is baked, roasted or popped prior to spray-coating.

12. A snack product prepared by spray-coating a baked, roasted, or popped substrate containing starch with a fat composition comprising at least 50% triglycerides bearing both long, saturated fatty acid residues derived from fatty acids having between 16 and 22 carbons, and short acid residues derived from acids selected from the group consisting of propionic acid, mixtures of acetic acid and propionic acid, butyric acid, mixtures of acetic acid and butyric acid, mixtures of propionic acid and butyric acid, and mixtures of acetic acid, propionic acid, and butyric acid.

13. A product according to claim 12 wherein the fat composition has a solid fat index of at least about 50% at 70° F. and at least about 40% at 80° F.

14. A product according to claim 11 wherein the fat composition has a solid fat index of at least about 60% at 70° F. and at least about 50% at 80° F.

15. A product according to claim 12 wherein at least about 75% of the long acid residues in the fat composition are derived from stearic acid.

16. A product according to claim 15 wherein the short acid residues in the fat composition comprise a mixture of acetic and propionic acid residues.

17. A product according to claim 15 wherein the short acid residues are derived from butyric acid.

18. A method for adhering seasonings to a food product comprising preparation sequences selected from the group consisting of:
(i) spraying the food product with triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F., and then dusting the seasonings onto the food product;
(ii) dusting seasonings onto a food product and then spraying the dusted food product with triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F.; and
(iii) mixing seasonings with triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F., and spraying the seasoning-oil mixture onto the food product.

19. A method according to claim 18 wherein a second coating of triglycerides is applied to the food product after the seasoning adhering sequence is carried out.

20. A method according to claim 18 wherein at least about 75% of the long acid residues are stearic acid residues.

21. A method according to claim 18 wherein the seasonings contain salt.

22. A method according to claim 18 comprising the steps of spraying the food product with triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F., and then dusting the seasonings onto the food product.

23. A method according to claim 18 comprising the steps of dusting seasonings onto a food product and then spraying the dusted food product with triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F.

24. A method according to claim 18 comprising the steps of mixing seasonings with triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F., and spraying the seasoning-oil mixture onto the food product.

25. A method for minimizing or eliminating the greasy handfeel of snack products spray-coated with a warm spray oil composition after baking, roasting, or popping, comprising formulating the spray oil with at least about 50% triglycerides bearing both long, saturated fatty acid residues derived from $C_{16}$ to $C_{24}$ fatty acids, and short acid residues derived from the group consisting of acetic acid, propionic acid, butyric acid, and mixtures of these, provided that the triglycerides have a solid fat index of at least about 50% at 70° F. and at least about 40% at 80° F.

26. A method according to claim 25 wherein the spray oil consists essentially of the triglycerides.

27. A method according to claim 25 wherein the triglycerides have a solid fat index of at least about 60% at 70° F. and at least about 50% at 80° F.

28. A method according to claim 27 wherein at least about 75% of the long residues are stearic acid residues.

* * * * *